United States Patent [19]

Obermeier

[11] 4,029,642

[45] June 14, 1977

[54] PROCESS FOR THE MANUFACTURE OF HUMAN INSULIN

[75] Inventor: Rainer Obermeier, Hattersheim, Main, Germany

[73] Assignee: Hoechst Aktiengesellschaft, Frankfurt am Main, Germany

[22] Filed: Dec. 19, 1975

[21] Appl. No.: 642,399

[30] Foreign Application Priority Data

Dec. 21, 1974 Germany ........................ 2460753

[52] U.S. Cl. .................. 260/112.7; 260/112.5 R
[51] Int. Cl.² ........................................ C07C 103/52
[58] Field of Search ........................ 260/112.7

[56] References Cited

UNITED STATES PATENTS

| 3,847,892 | 11/1974 | Wang | 260/112.7 |
|---|---|---|---|
| 3,903,068 | 9/1975 | Ruttenberg | 260/112.7 |
| 3,907,765 | 9/1975 | Wang | 260/112.7 |

OTHER PUBLICATIONS

Scientia Sinica, vol. 16, (1973), 61–70.
Hoppe—Seyler's Z. Physiol. Chem., Bd. 357, 5, 187–200, (1976).
Human Insulin: (1972), pp. 623–626.

*Primary Examiner*—Delbert R. Phillips
*Attorney, Agent, or Firm*—Curtis, Morris & Safford

[57] ABSTRACT

A process for the manufacture of human insulin by the condensation of porcine des-$B_{23-30}$ octapeptide insulin with a peptide and subsequent splitting-off of the protective groups by treatment with trifluoroacetic acid or with alkali.

1 Claim, No Drawings

PROCESS FOR THE MANUFACTURE OF HUMAN INSULIN

The present invention relates to a process for the manufacture of human insulin which comprises condensing des-$B_{23-30}$-octapeptide porcine insulin of the general formula (I)

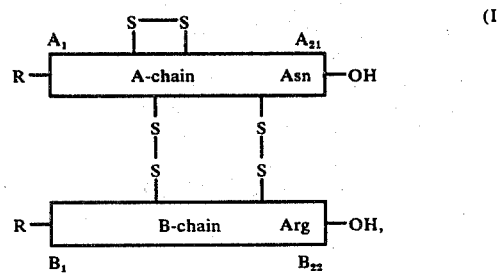

in which R stands for an amino protective group capable of being split off by proton solvolysis of β-elimination, with a peptide of the formula (II)

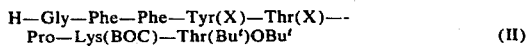

In which X stands for hydrogen or the tert.-butyl group, and splitting off the protective groups by a treatment with trifluoro-acetic acid or, optionally, an alkaline agent.

R may be preferably the tert.-butyloxy-carbonyl (Boc) group, the tert.-amyloxy-carbonyl (Aoc) group or the methylsulfonylethoxy-carbonyl (Msc) group.

Various suggestions have been made to use fragments of naturally occurring peptides or proteins for the semi-synthesis of peptides. For example in Science 177 (1972), page 623, the conversion of porcine insuline into human insulin has been described.

These two insulins only differ in the C-terminal amino acid of the B-chain. Since in the C-terminal range of the B-chain, there is an arginyl-glycine bond liable to be split by trypsin, the idea was obvious to use the already-known des-$B_{23-30}$-octapeptide insulin (porcine) (cf. Biochem. Biophys. Acta 133 (1967), page 219) as a starting product and introduce, instead of the split-off octapeptide, a synthetically prepared derivative corresponding to the amino-acid sequence of human insulin containing threonine instead of alanine in the $B_{30}$-position as disclosed in Science 177, page 623.

According to the hitherto known state of the art of peptide synthesis, functional groups, especially carboxy and amino groups, which were not allowed to react, had to be protected in a reversible and adequate manner.

The protection of the amino groups $A_1$ and $B_1$ in the des-$B_{23-30}$-octapeptide insulin as well as the protection of the functional groups in the synthetically prepared octapeptide are not problematic. However, des-$B_{23-30}$-octapeptide insulin contains, in addition to the carboxy group linked to the $B_{22}$-arginine group, five further carboxy groups at which simultaneous reactions were to be expected. These reactions would have led to an inseparable mixture of various derivatives, and therefore the carboxy groups had to be protected for the purpose of the known method.

To make sure of this, porcine insulin was converted in known manner (Biochem. J. 68 (1961), page 114) into the hexamethyl ester using diazomethane.

The arginyl-glycine compound was then split by means of trypsin, whereby the carboxy group linked at Arg-$B_{22}$ was set free. After the amino groups of des-$B_{23-30}$-octapeptide insulin pentamethyl ester had been protected by the tert.-butyloxycarbonyl group, condensation was performed with the amino group of the synthetically prepared, protected octapeptide having the sequence of human insulin. After the protective groups had been split off and alkaline saponification had been carried out, crude human insulin was obtained.

However, it has not yet been possible to reproduce the known synthesis described above, to give the indicated result.

The process of the present invention now permits a semisynthesis of human insulin in an entirely new and surprising manner. The N α $^{A}$1, N α $^{B}$1-bis-BOC derivative of the known des-$B_{23-30}$-octapeptide porcine insulin (formula I, R being Boc) is reacted directly with 1 equivalent of octapeptide of the human insulin sequence (formula II), using as condensation agent dicyclohexyl carbodiimide in a slight deficiency in the presence of 1-hydroxy benzotriazole.

Surprisingly, this reaction yields 20 to 30% of the human insulin derivative. Part of the des-octapeptide insulin remains unreacted. As a byproduct, a peptide having 59 amino acids (pentaconta-peptide), in which an additional condensation reaction of the octapeptide with the carboxy group of asparagine $A_{21}$ has taken place, is obtained.

The surprising feature of this reaction is that at first only the carboxy group of arginine $B_{22}$ reacts. Only then and far more slowly, the carboxy group of asparagine $A_{21}$ follows in the reaction. The four further carboxy groups present in the insulin do not react to a discernible extent under these conditions.

Since, according to this reaction, the carboxy groups need not be protected, the insulin is not damaged either during the esterification reaction or during the alkaline saponification. Owing to their different molecular size and atomic number, unreacted des-octapeptide and the pentacontapeptide can easily be separated by partition chromatography using Sephadex -LH 20 in a system of n-butanol/glacial acetic acid/water (2:1:10) or by gel chromatography using Sephadex -G 75 G 50 "superfine". The recovered des-octapeptide taken into regard, the yield of human insulin amounts to 30 – 40%.

To split off the protective tert.-butyl groups, the reaction product need only be treated with trifluoroacetic acid over 30 to 60 minutes at room temperature. This reaction does not damage insulin. When the methylsulfonylethyloxy-carbonyl group is chosen as the N-protective group, splitting-off by β-elimination requires a treatment with alkali, but the reaction conditions (0.1N NaOH, 0° C, 5 sec.) are such as not to damage insulin. The N α $^{A}$1, N α $^{B}$1-bis-BOC-des-$B_{23-30}$-octapeptide insulin (porcine) used as a starting product is prepared in the following manner:

Porcine insulin is reacted in a mixture of dimethylformamide, dimethyl sulfoxide and water, in the presence of N-ethylmorpholine, with excess tert.-butyloxycarbonyl-N-hydroxy-succinimide ester to yield the N α $^{A}$1, N α $^{B}$1, N ε $^{B}$29-tris-BOC insulin to be expected. To the solution of this compound in dimethylformamide and a tris(hydroxymethyl)amino-methane buffer solution (pH 7.5), trypsin is added in small portions until no more starting product is established by electrophoresis. The N α A1, N α B1-bis-BOC-des-B23-30-octapeptide insulin is then purified by partition chromatography using Sephadex LH 20 in a system of n-butanol/glacial acetic acid/water (2:1:10). This compound is then reacted with 1 mol of the peptide of formula II, prepared in known manner according to methods of peptide chemistry, 1 to 2 mol/l of 1-hydroxy-benzotriazole and about 0.9 mol/l of dicyclohexyl-carbodiimide in dimethylformamide at a pH of about 7 to 8 (cf. Chem. Ber. 103 (1970), page 788).

The crude product is purified as described above by partition chromatography and freed from the protective groups by treating it with trifluoroacetic acid-/anisole (5+1) over 60 minutes at room temperature. After precipitation with ether, equipotential precipitation from water at pH 5.4 and chromatography on Sephadex -G 75 or G 50 superfine, the compound is pure as established by electrophoresis and may be crystallized in known manner. The human insulin thus obtained has its full biological activity.

The human insulin prepared according to the process of the invention serves as a medicament for the treatment of diabetes mellitus in human patients, for example in cases where there is resistance to bovine and porcine insulins.

The following Example illustrates the invention.

EXAMPLE

Preparation of human insulin

5 Grams of porcine insulin were dissolved in 40 ml of dimethylformamide, 25 ml of dimethyl-sulfoxide, 0.5 ml of N-ethylmorpholine and 2.5 ml of water. While stirring, 1.5 g of tert.-butyl-oxycarbonyl-N-hydroxysuccinimide were added at room temperature, and the mixture was allowed to react for 6 hours. The reaction was interrupted by adding a drop of glacial acetic acid. The product was precipitated with ether and suction-filtered.

The residue was dissolved in 360 ml of dimethylformamide and diluted with 320 ml of tris-buffer solution (0.05 M, 0.01M on $CaCl_2$, pH 7.5). At 36° C, portions of 20 mg of trypsin each were added at intervals of 1 hour each.

After a total of 12 portions had been added, the pH was adjusted to 4.5 by means of acetic acid, and the solution was evaporated. The subsequent purification of the material in a Sephadex -LH 20 column (8 × 200 cm) by partition chromatography in a system of n-butanol/glacial acetic acid/water (2:1:10) yielded 3.25 g of N α A1, N α B1-bis-BOC-des-B23-30-octapeptide insulin (porcine), which no longer showed any starting material by an acidic and basic electrophoresis. The analysis of amino acids of the substance was correct. After a tentative splitting-off of the BOC groups, no insulin activity was any longer established. This material (3.25 g) was dissolved together with 100 mg of 1-hydroxy-benzotriazole, 750 mg of HCl.Gly-Phe-Phe-Tyr(Bu$^t$)-Thr-Pro-Lys(BOC)-Thr(Bu$^t$)-OBu$^t$ and 0.5 ml of N-ethylmorpholine in 30 ml of dimethylformamide. At room temperature, 120 mg of dicyclohexyl-carbodiimide were added, and the reaction mixture was stirred for 24 hours. The precipitated dicyclohexyl urea was suction-filtered, and the product was precipitated by adding ether. The precipitate was suction-filtered, washed with ether and dried. The substance was prepurified by partition chromatography using Sephadex -LH 20 in the above-mentioned system. 2.6 Grams of material obtained from the main-peak fraction were isolated by precipitation with acetone/ether. The dried, still protected derivative was allowed to react with a mixture of 5 ml of trifluoroacetic acid and 1 ml of anisole over 60 minutes at room temperature. The crude substance was then precipitated from the ice-cooled solution by adding ether. The dried precipitate was dissolved in water, precipitated with aqueous ammonia at pH 5.4 and centrifuged. The product was purified in 10% acetic acid on Sephadex -G 50 superfine or G 75. The human insulin could be isolated from the fractions of the desired peak by lyophilization. (Yield after crystallization: 1.2 gms.) The so-obtained human insulin showed 24 IU/mg in the biological test.

The octapeptide of formula I was prepared according to the following condensation scheme by the usual condensation methods:

Synthesis scheme for the octapeptide of formula (II)

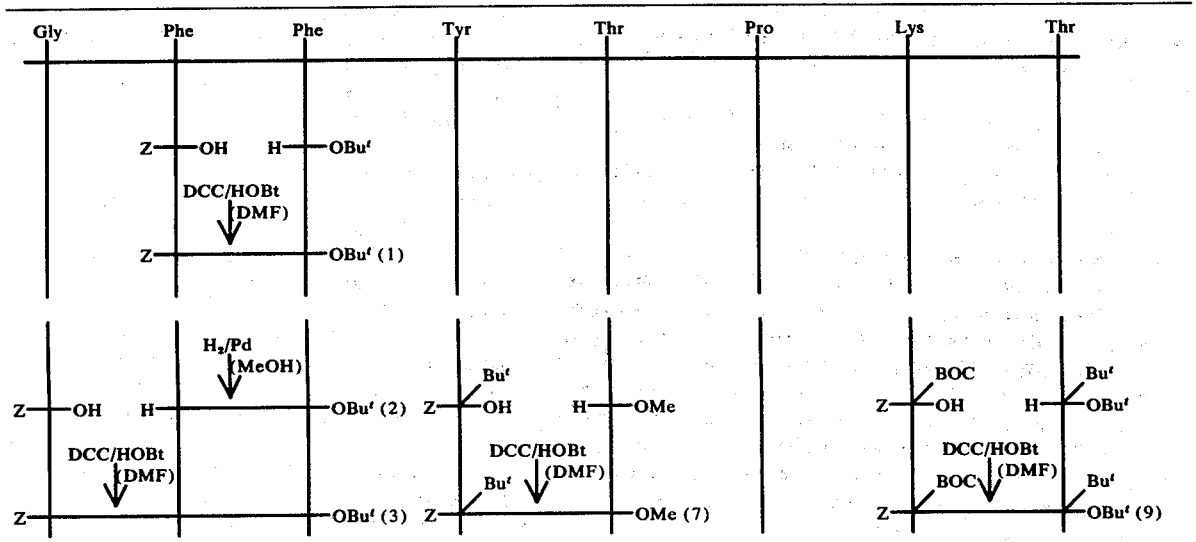

Synthesis scheme for the octapeptide of formula II

-continued
Synthesis scheme for the octapeptide of formula II

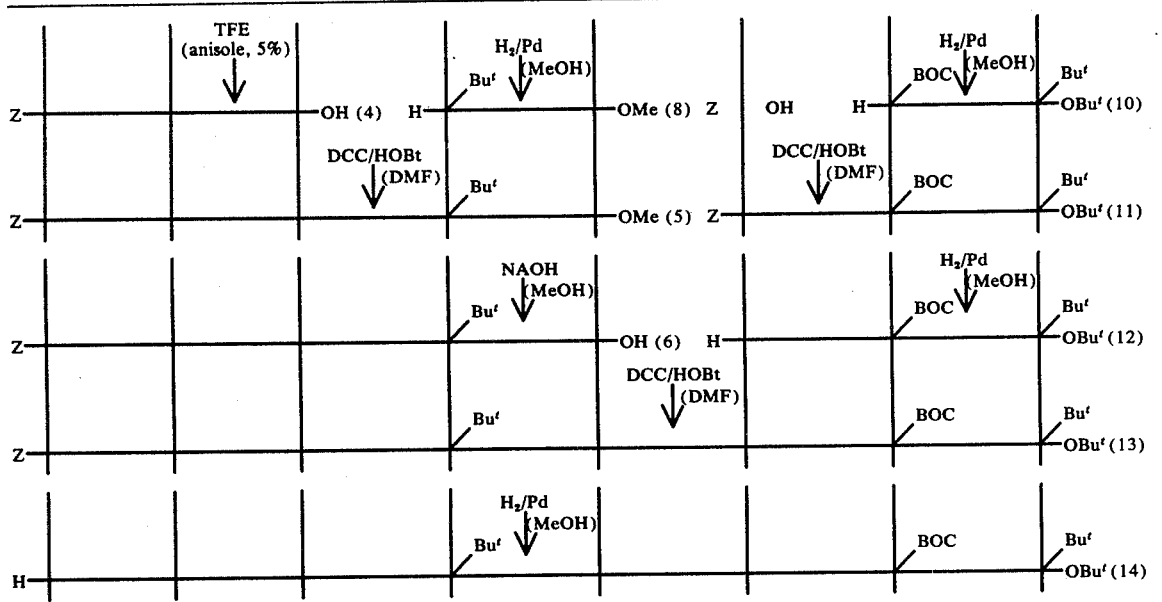

Physical properties of the intermediate products according to reaction scheme of page 9:

|      | M.p.          | $[\alpha]_D$ |                   |
|------|---------------|--------------|-------------------|
| (1)  | 93 – 95° C    | + 5.9        | c = 1/MeOH        |
| (2)  | 139 – 141° C  |              |                   |
| (3)  | 117 – 118° C  | −10.3        | c = 1/MeOH        |
| (4)  | 180 – 181° C  |              |                   |
| (5)  | solidifed oil | −23.9        | c = 1/MeOH/THF 5:1 |
| (6)  | solidified oil| −24.3        | c = 1/MeOH        |
| (7)  | solidified oil| − 8.1        | c = 1/MeOH        |
| (8)  |               | + 3.1        | c = 1/MeOH        |
| (9)  | oil           |              |                   |
| (10) | oil           |              |                   |
| (11) | oil           |              |                   |
| (12) |               | −30.9        | c = 1/MeOH        |
| (13) |               | −37.7        | c = 1/MeOH        |
| (14) |               | −50.7        | c = 1/MeOH        |

The analysis of amino acids and elementary analysis corresponds to those of the theory.

I claim:

1. A method for making human insulin, which comprises condensing des-$B_{23-30}$-octapeptide porcine insulin of the formula

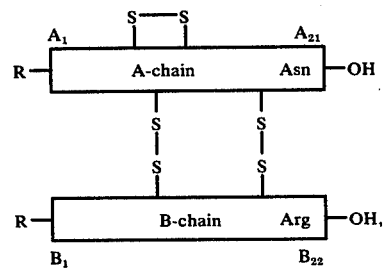

wherein R is an amino-protective group which is tert.-butyloxy-carbonyl, tert.-amyloxy-carbonyl, or methyl-sulfonyl-ethyloxy-carbonyl with a peptide of the formula H—Gly—Phe—Phe—Tyr(X)—Thr(X)—
Pro—Lys(BOC)—Thr(Bu$^t$)OBu$^t$, wherein X is hydrogen or tert.-butyl, in the presence of dicyclohexyl carbodiimide and hydroxybenzotriazole, and then splitting off said amino-protective group with alkali if said group is methylsulfonyl-ethyloxy-carbonyl or with trifluoroacetic acid if said protective group is tert.-butyloxy-carbonyl or tert.-amyloxy-carbonyl.

* * * * *